(12) United States Patent
Hirsch

(10) Patent No.: US 9,539,074 B2
(45) Date of Patent: Jan. 10, 2017

(54) PACKAGE FOR AN ORTHODONTIC BRACKET

(71) Applicant: PBD, Patent Business & Development AG, Zug (CH)

(72) Inventor: Markus Hirsch, Klagenfurt-Viktring (AT)

(73) Assignee: PDB, Patent & Business Development AG, Zug (CH)

( * ) Notice: Subject to any disclaimer, the term of this patent is extended or adjusted under 35 U.S.C. 154(b) by 0 days.

(21) Appl. No.: 14/508,024

(22) Filed: Oct. 7, 2014

(65) Prior Publication Data

US 2016/0095682 A1    Apr. 7, 2016

(51) Int. Cl.
| | |
|---|---|
| *B65D 25/10* | (2006.01) |
| *A61C 19/02* | (2006.01) |
| *A61C 7/16* | (2006.01) |
| *B65D 43/02* | (2006.01) |
| *A61C 7/14* | (2006.01) |

(52) U.S. Cl.
CPC ............ *A61C 19/02* (2013.01); *A61C 7/14* (2013.01); *A61C 7/16* (2013.01); *B65D 25/10* (2013.01); *B65D 43/02* (2013.01); *A61C 2202/00* (2013.01); *A61C 2202/01* (2013.01)

(58) Field of Classification Search
CPC ....... A61C 19/02; A61C 7/16; A61C 2202/01; B65D 25/10; B65D 43/02
USPC ................................. 206/63.5, 438, 368, 369
See application file for complete search history.

(56) References Cited

U.S. PATENT DOCUMENTS

| | | | |
|---|---|---|---|
| 673,019 A | 4/1901 | Gilbert | |
| 2,412,352 A | 12/1946 | Myerson | |
| 2,897,593 A | 8/1959 | Hollander et al. | |
| 3,899,379 A | 8/1975 | Wanesky | |
| 3,988,196 A | 10/1976 | Wanesky | |
| 4,978,007 A | 12/1990 | Jacobs et al. | |
| 4,979,611 A | 12/1990 | Bolliger et al. | |
| 5,348,154 A | 9/1994 | Jacobs et al. | |
| 5,538,129 A | 7/1996 | Chester et al. | |
| 5,575,645 A | 11/1996 | Jacobs et al. | |
| 6,779,657 B2 * | 8/2004 | Mainwaring et al. | ........ 206/229 |
| 6,799,969 B2 | 10/2004 | Sun et al. | |
| 6,843,370 B2 | 1/2005 | Tuneberg | |

(Continued)

FOREIGN PATENT DOCUMENTS

| | | |
|---|---|---|
| WO | 2010126716 A1 | 11/2010 |
| WO | 2013162975 A1 | 10/2013 |

*Primary Examiner* — King M Chu
(74) *Attorney, Agent, or Firm* — Collard & Roe, P.C.

(57) ABSTRACT

A package for an orthodontic bracket or other dental product is formed by a container having a bottom and a plurality of sidewalls, creating a cavity within the container. One of the sidewalls is disposed at an angle greater than 90 degrees from the bottom so that it slants up and away from the bottom. This way, the opening in the top of the package is larger than the surface area of the bottom of the package. There is a removable top configured for covering the cavity. There is a quantity of pliable material attached to the bottom or to the slanted sidewall. The pliable material is configured to be able to hold a small object such as an orthodontic bracket in place when the object is pressed into the pliable material. The bracket is placed on the pliable material in such a way that adhesive disposed on the rear side of the bracket does not touch the pliable material or any other part of the bracket.

11 Claims, 3 Drawing Sheets

(56) References Cited

U.S. PATENT DOCUMENTS

| | | |
|---|---|---|
| 7,381,053 B2 | 6/2008 | Tuneberg |
| 7,469,783 B2 | 12/2008 | Rose, Sr. |
| 7,726,470 B2 | 6/2010 | Cinader, Jr. et al. |
| 7,841,464 B2 | 11/2010 | Cinader, Jr. et al. |
| 2003/0196914 A1 | 10/2003 | Tzou et al. |
| 2005/0016884 A1 | 1/2005 | Stout et al. |
| 2008/0179201 A1* | 7/2008 | Hess et al. .................. 206/83 |
| 2008/0286710 A1* | 11/2008 | Cinader et al. ............... 433/9 |
| 2012/0273371 A1 | 11/2012 | Bathen et al. |
| 2013/0075282 A1 | 3/2013 | Cinader, Jr. et al. |

\* cited by examiner

PACKAGE FOR AN ORTHODONTIC BRACKET

BACKGROUND OF THE INVENTION

1. Field of the Invention

The present invention relates to a package for a pre-pasted orthodontic bracket. In particular, the invention relates to a package that supports the bracket in place while keeping the pre-pasted portion free from contact with any surface of the package.

2. The Prior Art

Modern orthodontic techniques include repositioning teeth that are misaligned, too close together or otherwise mis-positioned. In order to reposition the teeth, the teeth are connected to an arch wire that serves as a guide, urging the teeth into the desired position and orientation. In order to connect the teeth to the arch wire, small brackets with slots for receiving the arch wire are attached to the teeth. The brackets are usually attached to a patient's teeth by means of an adhesive.

Applying an appropriate amount of adhesive to the base of a bracket can be a time consuming and tedious. Too little adhesive may result in the bracket coming loose from the tooth after installation, while excessive amounts of adhesive will be pushed out from between the bracket and tooth, requiring removal. Further, while two-part chemically curing adhesive systems are available for bonding orthodontic brackets to a patient's teeth, many practitioners prefer photo sensitive adhesives that are cured upon exposure to light in the visible spectrum for a relatively short period. Consequently, time is also a factor insofar as the adhesive applied to the bracket can only be exposed to visible light for a limited period before the bracket is positioned on the tooth.

In order to address these issues, pre-pasted orthodontic appliances were developed. Pre-pasted orthodontic appliances have an adhesive, normally a photo sensitive, light curing adhesive, applied to the base of the bracket before the bracket is packaged. Pre-pasted brackets reduce the amount of time required to install brackets on the patient's teeth by eliminating the need for the orthodontist to apply the adhesive to the bracket. Pre-pasted brackets also reduce the amount of wasted adhesive as the manufacturer can precisely control the amount and placement of the adhesive on the base of the bracket.

Packaging for brackets with a pre-applied light curing adhesive must protect the adhesive from exposure to light, as well as from contamination and evaporation. Further, if the adhesive adheres to the package, the adhesive coating may be disturbed when the bracket is removed from the package. In addition, the package should present the bracket to the orthodontist in a fashion that facilitates quick and convenient removal of the bracket from the package. For example, U.S. Pat. No. 7,381,053 discloses a package for a pre-pasted orthodontic bracket in which the bracket is suspended on a skirt that holds the bracket above the bottom of the packaging. U.S. Pat. No. 4,978,007 shows a package where the bracket is suspended on a jig that extends across a cavity in the package, so that the adhesive does not contact the bottom of the package.

While these packages prevent the adhesive from contacting the walls of the packaging, they are expensive and cumbersome to produce, usually requiring several different parts that have to be assembled.

SUMMARY OF THE INVENTION

It is therefore an object of the invention to provide a packaging for prepasted orthodontic brackets that is simple and inexpensive to produce, yet protects the adhesive-covered side of the bracket from contact.

This object is accomplished according to the invention by a package for an orthodontic bracket formed by a container having a bottom and a plurality of sidewalls, creating a cavity within the container. One of the sidewalls is disposed at an angle greater than 90 degrees from the bottom so that it slants up and away from the bottom. This way, the opening in the top of the package is larger than the surface area of the bottom of the package. There is a removable lid configured for covering the cavity. This lid is preferably permanently connected on one end and then removably adhered to the package surrounding the cavity with a suitable adhesive. The lid can then be peeled up from the cavity, when access to the cavity is desired. Alternatively, the lid can be configured to be held onto the package with a snap-fit.

There is a quantity of pliable material attached to the bottom or to the slanted sidewall. The pliable material is configured to be able to hold a small object in place when the object is pressed into the pliable material. The pliable material is preferably formed from wax, but other materials, such as soft plastics, water solvable glue or adhesives, could be used. In one embodiment, the pliable material is attached to the slanted sidewall, and the slanted sidewall has an indentation for accommodating the pliable material such that the pliable material lies flush with the sidewall. This also keeps the pliable material in place within the package.

In one embodiment, there is a top surface extending around the cavity, creating a lip for the lid. The removable lid covers the top surface and is attached at one end to an edge of the top surface. A support wall can be configured to extend down from the top surface and face the slanted sidewall to prevent the package from tipping over when placed on a flat surface.

The package is ideally configured for supporting an orthodontic bracket. In use, the bracket is pushed into the pliable material in an orientation such that the adhesive side is facing away from or perpendicular to the pliable material. This way, the adhesive side is protected from contact with any of the side walls, bottom or cover of the package. Once the lid is adhered in place, a sealed package for the bracket is created.

BRIEF DESCRIPTION OF THE DRAWINGS

Other objects and features of the present invention will become apparent from the following detailed description con-sidered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
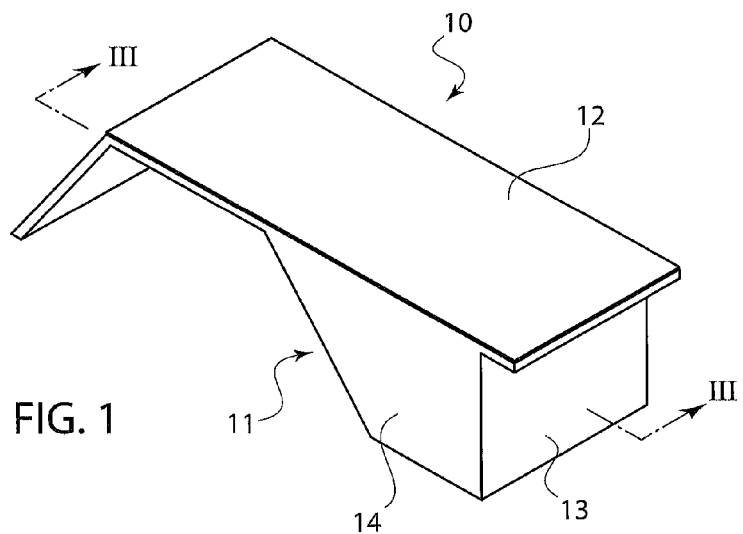
FIG. 1 shows the package according to the invention in a sealed configuration.
Figure 2:
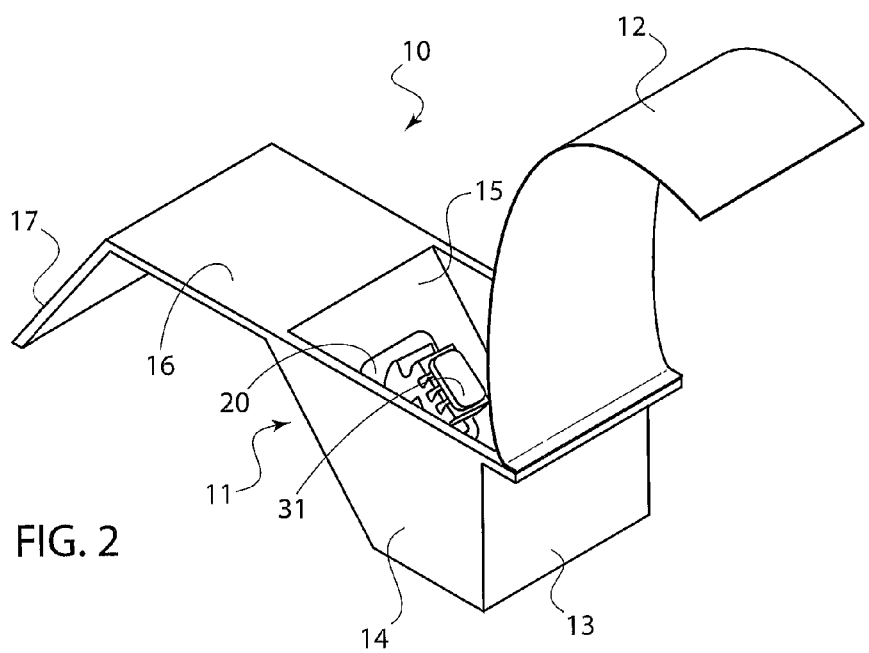
FIG. 2 shows the package with the cover open and a bracket mounted therein.

Referring now in detail to the drawings, a package 10 is shown, which comprises a container 11 having a front wall 13, side walls 14, a rear wall 15 and a bottom 18. Rear wall 15 is configured to extend up from bottom 18 at an angle greater than 90 degrees, in this case approximately 135 degrees, so that the opening created in the top of container 11 is greater in surface area than the surface area of bottom 18. Other angles of either greater or smaller than 90 degrees could also be used. A removable lid 12 is placed over the top of container 11 to seal the cavity created by the sidewalls. Lid 12 is preferably configured of a flexible material, such as plastic or metal such as aluminum, on which identification printing can be applied via printing or lamination. Lid 12 is secured with adhesive around the perimeter of the cavity, and permanently connected to container 11 at one edge, so that it can be peeled back to gain access to the interior of container 11. A top surface 16 extends out from the top edges of the side, front and rear walls. A support wall 17 extends down from an edge of top surface 16 to add stability to container 11. In addition, a lip 19 extends out in an opposite direction from top surface 16 to provide an additional surface for contact of lid 12.

Figure 3:
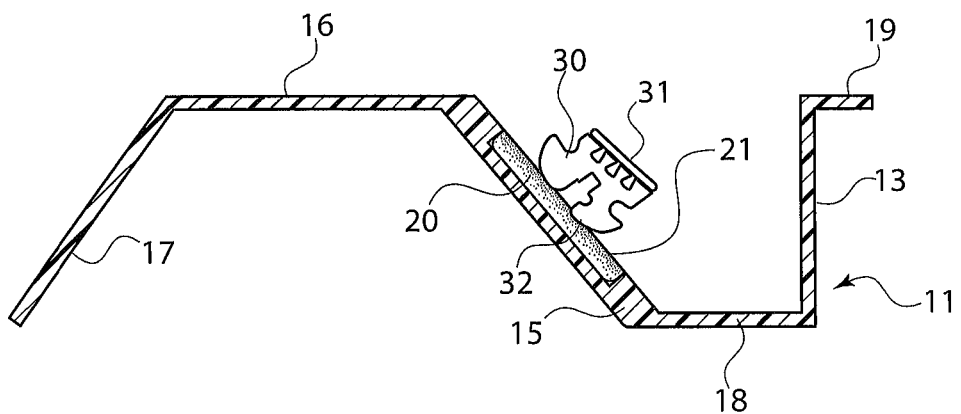
FIG. 3 shows a side cross-sectional view along lines III-III of FIG. 1
Figure 4:
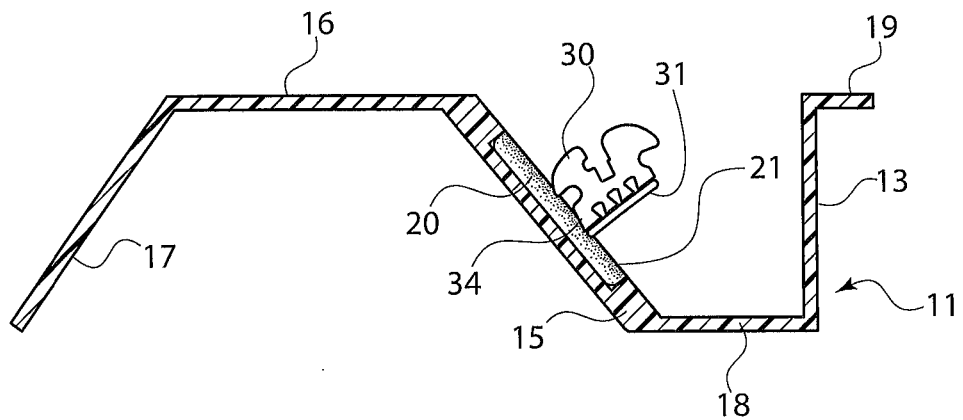
FIG. 4 shows a side cross-sectional view of an alternative arrangement of the bracket as shown in FIG. 3.

As shown in FIGS. 3 and 4, rear wall 15 has an indentation 21 for accommodating an amount of a pliable material 20. Pliable material 20 can be wax or any other suitable material. Material 20 is placed in indentation 21 so that its top surface is flush with rear wall 15. Alternatively, rear wall 15 can have no indentation and pliable material 20 can be placed directly on flat wall 15. Pliable material 20 is held in place via an additional adhesive or by its own adhesive properties. A sufficient amount of pliable material is used so that when the object to be secured is pressed into the pliable material, the pliable material molds around portions of the object and holds it in place. Thus, the pliable material is more than a simple adhesive, but holds the object in place via physical force as well.

An orthodontic bracket 30 can then be positioned within container 11 by pressing bracket 30 into pliable material 20 until bracket 30 stays in place. As shown in FIG. 3, bracket 30 can be positioned so that front surface 32 is pressed into pliable material 20 and the rear surface, which contains a quantity of adhesive 31, faces away from pliable material 20.

Alternatively, as shown in FIG. 4, a side surface 34 of bracket 30 can be pressed into pliable material 20, so that the rear of the bracket with adhesive 31 is positioned at a right angle to the rear wall 15. As another alternative (not shown), pliable material 20 can be placed on the bottom surface 18 of package 11.

Figure 5:
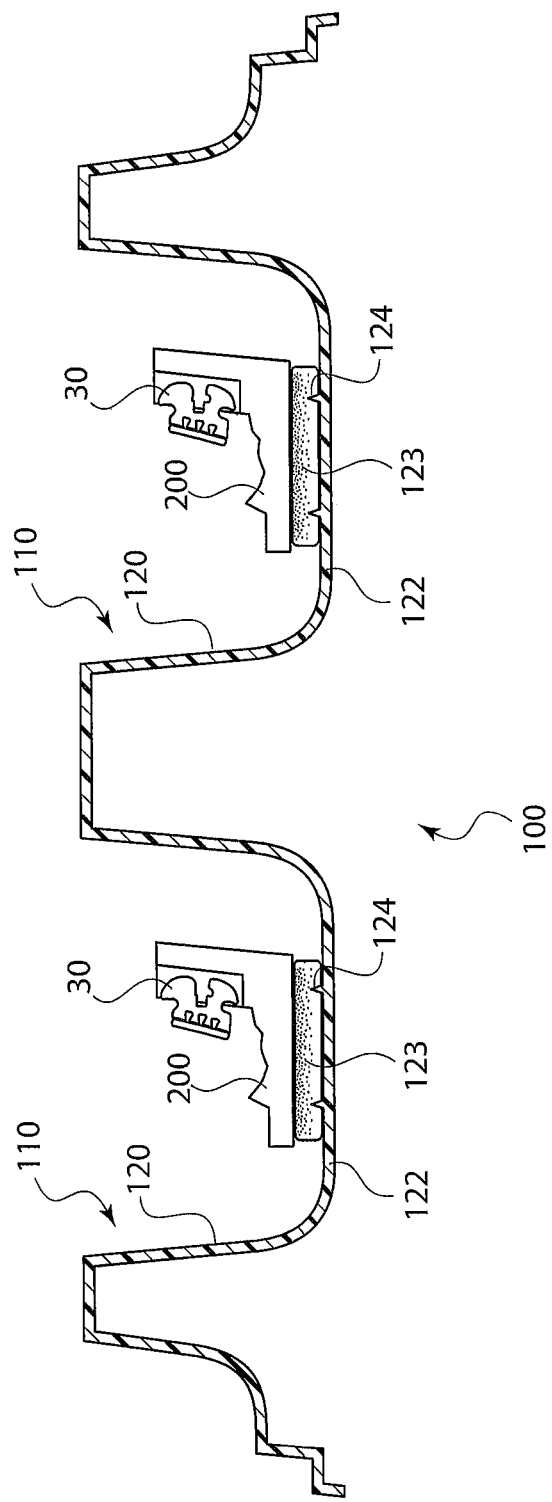
FIG. 5 shows a side cross-sectional view of an alternative embodiment of the invention.

FIG. 5 shows an alternative embodiment of the invention. Here, package 100 contains two integrally molded containers 110, each having side walls 120 and a bottom 122. An amount of pliable material 123 is secured onto bottom 122 with the help of ridges 124. A jig 200 for holding an orthodontic bracket 30 is then secured into pliable material 123 for storage and shipping. In use, the technician merely has to lift jig 200 off of pliable material 123 and place bracket 30 onto the desired tooth. Bracket 30 can be pre-pasted or can be shipped without adhesive.

The present invention provides a novel, convenient and inexpensive way to package small items, including pre-pasted orthodontic brackets. It does not require jigs, support systems or any type of multi-piece configuration, as the pliable material is sufficient to keep the bracket in place during transport.

Accordingly, while only a few embodiments of the present invention have been shown and described, it is obvious that many changes and modifications may be made thereunto without departing from the spirit and scope of the invention.

What is claimed is:

1. A package for an orthodontic bracket, comprising:
   at least one container having a bottom and a plurality of sidewalls, creating a cavity within the container, one of said sidewalls being disposed at an angle of between 45 and 180 degrees from the bottom,
   a removable lid configured for covering the cavity, and
   a quantity of pliable material attached to said one sidewall disposed at an angle between 45 and 180 degrees from the bottom,
   wherein the quantity of pliable material is configured to support a dental or orthodontic product when the product is pressed into the pliable material, and
   wherein said one sidewall disposed at an angle between 45 and 180 degrees from the bottom has an indentation for accommodating the quantity of pliable material such that the quantity of pliable material lies flush with the sidewall.

2. The package according to claim 1, wherein the quantity of pliable material is wax.

3. The package according to claim 1, further comprising a top surface extending around the cavity, wherein the removable lid covers the top surface and wherein the removable cover is permanently attached at one end to an edge of the top surface.

4. The package according to claim 1, wherein the removable lid is connected to the container via adhesive.

5. The package according to claim 3, further comprising a support wall extending from the top surface and facing said one sidewall disposed at an angle between 45 and 180 degrees from the bottom.

6. The package according to claim 1, further comprising at least one orthodontic bracket embedded in said quantity of pliable material.

7. The package according to claim 6, wherein the at least one bracket has one side covered with applied adhesive.

8. The package according to claim 7, wherein the adhesive is curable with actinic radiation.

9. The package according to claim 7, wherein the bracket is pressed into the quantity of pliable material so that the side carrying the adhesive is disposed facing away from the pliable material.

10. The package according to claim 7, wherein the bracket is pressed into the quantity of pliable material so the side carrying the adhesive is disposed at a right angle to said quantity of pliable material.

11. The package according to claim 1, wherein the package contains at least two containers.

* * * * *